United States Patent [19]
Kligman et al.

[11] 4,355,028
[45] * Oct. 19, 1982

[54] COMPOSITION FOR TREATING ACNE VULGARIS

[75] Inventors: Albert M. Kligman, Philadelphia, Pa.; Walter L. McKenzie, Williamsville; Peter F. Ciesla, Lancaster, both of N.Y.

[73] Assignee: Westwood Pharmaceuticals, Inc., Buffalo, N.Y.

[ * ] Notice: The portion of the term of this patent subsequent to Mar. 9, 1999, has been disclaimed.

[21] Appl. No.: 259,327

[22] Filed: Apr. 30, 1981

Related U.S. Application Data

[63] Continuation of Ser. No. 48,197, Jun. 13, 1979, abandoned, which is a continuation-in-part of Ser. No. 893,239, Apr. 4, 1978, Pat. No. 4,318,907.

[51] Int. Cl.³ .................... A61K 31/60; A61K 31/075

[52] U.S. Cl. .................................... 424/230; 424/235; 424/338

[58] Field of Search ........................ 424/230, 235, 338

[56] References Cited

U.S. PATENT DOCUMENTS 3,530,217  9/1970  White et al. ......................... 424/180
3,535,422 10/1970  Cox et al. ............................ 424/164

FOREIGN PATENT DOCUMENTS 2416542  4/1974  Fed. Rep. of Germany .

Primary Examiner—Leonard Schenkman
Attorney, Agent, or Firm—Morton S. Simon

[57] ABSTRACT

Procedure for treating acne vulgaris that uses salicylic acid and benzoyl peroxide either sequentially or simultaneously. Compositions for practicing each of these aspects of the invention are also described.

16 Claims, No Drawings

COMPOSITION FOR TREATING ACNE VULGARIS

This is a continuation of co-pending application Ser. No. 048,197, filed June 13, 1979, and now abandoned, which in turn was a continuation-in-part of co-pending application Ser. No. 893,239, filed Apr. 4, 1978 and which issued Mar. 9, 1982 as U.S. Pat. No. 4,318,907.

This invention relates to procedures for treating acne vulgaris that employ salicylic acid and benzoyl peroxide as active ingredients. It also concerns topical therapeutic compositions that are useful for this purpose and particularly stable compositions of this character.

The pathology of acne vulgaris is believed to involve a number of factors; the first of which is the formation of comedones more commonly referred to as whiteheads (closed comedones) and blackheads (open comedones). These are solid horny masses that plug follicles and are associated with increased production of sebum. They are made up of tightly packed keratinized cells. These plugs are white (whiteheads) when originally formed but through continued growth and deposition of the normal pigment, pigment melanin becomes blackheads.

As the comedo enlarges through continued accumulation of keratinized cells, pressure builds up within the follicles which eventually rupture, dumping the contents consisting of horny material, sebum and bacteria into the skin. This provokes inflammatory responses which take the form of pustules (pimples) when the rupture is small and cystic-nodules with complete rupture.

One of the prior art modes for the treatment of acne vulgaris has been the application of a keratolytic agent for the purpose of drying and peeling the skin to remove the keratinous plugs. The agents used for this purpose include sulfur, resorcinol, resorcinol monoacetate and salicylic acid. Hexachlorophene has also frequently been added for its antibacterial effect. (See "Handbook of Non-Prescription Drugs", 1969 Edition pages 118–121, published by the American Pharmaceutical Association, Washington, D.C. ). U.S. Pat. No. 3,530,217 also suggests that other antibacterial agents such as parachlorometaxylenol, tyrothricin, neomycin sulfate, benzalkonium chloride and Bithinonol may be used along with keratolytic agents such as sulfur, resorcinol, salicylic acid and benzoyl peroxide in the treatment of acne.

It has now been found that benzoyl peroxide and salicylic acid when used together at certain specified levels, exhibit a therapeutic effect greater than either agent alone in treating acne. These materials may be used in combination with each other in the treatment of acne or may be employed in a regimen of treatment in which one is applied after the other.

It is accordingly an object of this invention to provide procedures for the treatment of acne vulgaris that involve the use of salicylic acid and benzoyl peroxide at certain specified levels simultaneously (e.g. with both active ingredients in the same vehicle) or sequentially (e.g. with the active ingredients in separate vehicles).

It is also an object of this invention to provide compositions or articles of manufacture carrying salicylic acid and benzoyl peroxide at certain specified levels that are especially useful in the treatment of acne vulgaris.

It is still a further object of this invention to provide gel compositions which are chemically and physically stable (i.e. exhibit no degradation of active components or deterioration of the gel system) containing salicylic acid and benzoyl peroxide at certain specified levels that are useful in the treatment of acne vulgaris.

Other and more detailed objects of this invention will be apparent from the following description and claims.

Benzoyl peroxide is antimicrobial and suppresses the acne bacillus, *Propionibacterium acnes*, an organism which has an important causal role in acne vulgaris. Salicylic acid, on the other hand, is not just another keratolytic agent like resorcinol, phenol and other traditional agents which have been used to cause peeling. It belongs to a special class of comedolytic drugs which interfere with the formation of blackheads and whiteheads, horny masses which clog the follicles. Few keratolytic agents have this property, the other well-known one being vitamin A acid. Above and beyond the comedolytic effect, salicylic acid has other properties which add uniqueness to the present combination. It weakens the horny layer barrier, thereby increasing the permeability of skin to the benzoyl peroxide. As a result of its effect on the barrier, the tissue concentration of benzoyl peroxide is increased with a corresponding increase in efficacy. The combined therapeutic efficacy of benzoyl peroxide and salicyclic acid is considerably greater than the effect of each agent alone.

Salicylic acid has been suggested for use in combination with tars or mercury compounds in the treatment of psoriasis to enhance the penetration of these drugs. However, there has been no suggestion in the prior art that this would increase the antibacterial effect of benzoyl peroxide in the treatment of acne vulgaris.

It has been suggested in the prior art that the benzoyl peroxide is an effective keratolytic and antibacterial agent in the treatment of acne. In this connection, attention is directed to U.S. Pat. No. 3,535,422. This patent also suggests that the combination of precipitated sulfur and benzoyl peroxide produces greater keratolysis than either substance alone.

Although sulfur is widely regarded as keratolytic and antimicrobial, it has repeatedly been found that it enhances neither the comedolytic nor antibacterial actions of benzoyl peroxide. It has been reported that it actually encourages the formation of comedones. In a like fashion, 5% resorcinol in association with benzoyl peroxide has also been evaluated and no enhancement of therapeutic activity was evident.

The concentration of benzoyl peroxide and salicylic acid as employed in this invention is important. It has been found, for example, that 2.5% salicylic acid used in conjunction with 5% benzoyl peroxide was scarcely better than benzoyl peroxide alone in the treatment of acne vulgaris. On the other hand, 10% salicylic acid with 5% benzoyl peroxide caused excessive redness and peeling in about one third of subjects treated and therefore, is of little, if any, value in this connection.

The level of salicylic acid, in accordance with this invention, will generally be in the range of from about 3% to about 7% by weight based on the total weight of the composition; whereas, benzoyl peroxide will ordinarily be employed at concentrations in the range of from about 3% to about 20% on the same basis. Optimum results are obtained when both the salicylic acid and the benzoyl peroxide are each used at a level of about 5% by weight on the total weight of the composition.

The active ingredients employed in this invention may be applied from a variety of vehicles. In a typical sequential treatment, the salicylic acid is applied, for example as a 5% solution in a hydroalcoholic vehicle (e.g. 75% ethanol/25% water). This is followed by treatment with benzoyl peroxide applied, for example, as 5% benzoyl peroxide gel. In this procedure, the solution of salicylic acid applied to the acne lesions is permitted to dry on the skin and the 5% benzoyl peroxide gel is then immediately applied.

In another form of this invention, the salicylic acid and the benzoyl peroxide are applied simultaneously in the same vehicle, e.g. as a gel vehicle. These gels will ordinarily be aqueous gels containing gelling or thickening agents. As examples of such gelling or thickening agents, mention may be made of such materials as Veegum (magnesium aluminum silicate), sodium CMC, hydroxypropyl cellulose (e.g. Klucel HF), hydroxyethyl cellulose (Natrosol 250 HHR), methyl cellulose (Methocel A 4M); Carbopol 941 (neutralized with diisopropanolamine), etc. water dispersible starches (Nucol 4227) and mixtures thereof. The quantity of gelling or thickening agent that may be employed may vary somewhat. Ordinarily, it is comprised of about 0.1% to 5.0% by weight based on the total weight of the composition.

Although gel products of varying degrees of stability and viscosity may be prepared using any of the gelling agents suggested above, it has been a problem to develop a gel product that has a commercially acceptable stability, consistency and viscosity. A number of gelling agents were tried in an effort to prepare a commercially acceptable product. One was rejected because there resulted a destruction of the gel consistency and a separation of the suspended active ingredients. Another was rejected because it gave a thick lumpy mass which could not be dispersed even after considerable mixing. Still another, although it initially gave a satisfactory product, after several hours the viscosity dropped precipitously and this could not be considered commercially acceptable. In other instances, while the gelling agent selected provided a stable gel, it did not give a product having a commercially acceptable viscosity or smoothness.

Especially stable gel products of the present invention having the commercially requisite viscosity and texture are obtained by employing a mixture of a magnesium aluminum silicate (e.g. Veegum with methyl cellulose (methocel) as the gelling agent. Although the quantities of these agents may also vary somewhat in the preferred form of this invention, the magnesium aluminum silicate will preferably comprise from about 1.0 to 3.0% by weight based on the total weight of the composition; optimum results being obtained when the level of this material is at about 2.0% by weight. With regard to the Methocel component of the gelling agent, this may also vary. Good results are obtained with levels of Methocel in the range of from about 1.0 to 3% by weight based on the total weight of the composition. The best results are obtained when the magnesium aluminum silicate is at a level of about 2% by weight and the methocel is at a level of about 1.25% by weight. In any event, the combined total of magnesium aluminum silicate and Methocel will preferably not exceed about 5% by weight based on the total weight of the composition.

It has also been found that the texture, appearance as well as the chemical stability of the gel compositions of this invention, including those that contain both salicylic acid and benzoyl peroxide (e.g. see Example 2A below) may be enhanced by incorporating therein a "Cold Process Starch", i.e. a water soluble starch. Products of this character that are especially suited for the present purposes are sold under the tradename: NUCOL (e.g. NUCOL2 NUCOL 326 and particularly NUCOL 4227). These starch products may be present in the gel compositions of this invention in various quantities. However, generally it will be present in the range of from about 0.5% to about 2.0% by weight based on the total weight of the composition and preferably about 1.0%.

In general, benzoyl peroxide is chemically stable in the freshly prepared gel compositions encompassed in the present invention. However, when benzoyl peroxide is combined with salicylic acid in a gel composition that also contains laureth-4, this seems to affect the shelf-life of the product insofar as benzoyl peroxide is concerned. Cold process starches (e.g. Nucol 4227) aid in enhancing the physical stability of products of this character (e.g. the composition of Example 2A) and may also play a role in enhancing their chemical stability. This is illustrated in the chemical stability study summarized below. In this study, the various products were stored for the number of months indicated in column 1 at room temperature; 35° C. and 45° C. unless otherwise specified.

| Months | Benzoyl Peroxide Content % of Initial Assay | | |
|---|---|---|---|
| | Room Temperature | 35° C. | 45° C. |
| A. Benzoyl Peroxide 5% & Salicylic Acid 5% Gel (Example 2A) | | | |
| Zero | 100.0 | — | — |
| 1 | 99.5 | (100.4) | 98.2 |
| 2 | — | 94.7 | 92.9 |
| 4 | (100.2)[2] | (99.8) | — |
| B. Benzoyl Peroxide 5% & Salicylic Acid 5% Gel (Example 2) | | | |
| Zero | (100.0) | — | — |
| 1 | — | (84.9)[1] | — |
| 5 | (77.0) | — | — |
| C. Benzoyl Peroxide 5% Gel (Example 1, Composition B) | | | |
| Zero | 100.0 | — | — |
| 1 | — | 99.6 | 92.2 |
| 2 | 100.9 | 97.5 | 85.9[1] |
| 3 | 99.2 | 96.7 | — |

[1]Stability study discontinued at specified temperature since benzoyl peroxide content <90%
[2]( ) values in parenthesis are for product in glass containers. All other values are for product in 1¼ oz. plastic tubes (white Hd P/E)

Product A and C at room temperature exhibit no instability while Product B yields substantial (i.e. greater than 20%) loss in potency at 5 months. At elevated temperatures (35° C. and 45° C.) Product A yields good stability. Product B at 35° C. exhibits very poor stability with over 15% loss of potency at 1 month. Product C yields some instability at 45° C. while at 35° C. the stability is relatively good. Overall, the stability of Product A is far superior to Product B while being similar to Product C.

Salicylic acid and benzoyl peroxide are each sparingly soluble in water. As an optional feature, to facilitate the preparation of the aqueous gel composition and yield cleansing properties to the finished product, it is sometimes useful to employ a surface active agent. A variety of surface active agents may be employed for this purpose. Among these, mention may be made of such materials as laureth-4, sodium lauryl sulfate, dioctyl sodium sulfosuccinate, sodium laureth sulfate, sodium sulfoacetate. The quantity of surface active agent employed can also vary. Ordinarily, this will be in the range of from about 2.0% to 6.0% by weight based on the total weight of the composition.

If a surface active agent is employed, laureth-4 is a typical choice. Laureth-4 is the CTFA name for the ethoxylated ether of lauryl alcohol having the formula $CH_3(CH_2)_{10}CH_2(OCH_2CH_2)_nOH$ wherein n has an average value of 4. Laureth-4 may be used in the present composition in the range of from about 3.0% to 6.0% by weight based on the total weight of the composition. Optionally, this is present at a level of about 6.00% by weight.

Another surface active agent which may be employed is dioctyl sodium sulfosuccinate, the CTFA name for the sodium salt of the diester of an octyl alcohol and sulfosuccinic acid which conforms to the formula:

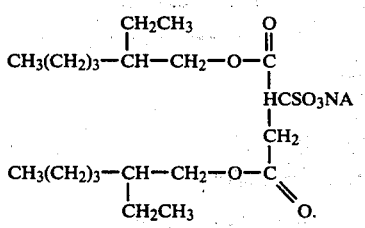

Dioctyl sodium sulfosuccinate may be used in the present composition in the range from about 0.5% to 3.0% by weight based on the total weight of the composition. Optionally, this is present at a level of about 1.0% by weight.

Another surface active agent which may be employed is sodium laureth sulfate, the CTFA name for the sodium salt of sulfated ethoxylated lauryl alcohol that conforms generally to the formula: $CH_3(CH_2)_{10}CH_2(OCH_2CH_2)_nOSO_3Na$ wherein n averages between 1 and 4.

Sodium laureth sulfate may be used in the present composition in the range from 3.0% to 6.0% by weight based on the total weight of the composition. Optionally, this is present at a level of about 4.0%.

Another surface active agent which may be employed is sodium lauryl sulfoacetate, the CTFA name for the organic salt that conforms generally to the formula:

$$CH_3(CH_2)_{10}CH_2OSO_2CH_2COO^-Na^+$$

Sodium lauryl sulfoacetate may be used in the present composition in the range from about 1.0% to 3.0% by weight based on the total weight of the composition. Optionally, this is present at a level of about 2.0% by weight.

However, under some circumstances, it is preferable to eliminate the surface active agent all together. Effective and stable gel preparations containing benzoyl peroxide and salicylic acid at the required levels have been prepared without using any surface active agent.

Other ingredients commonly contained in aqueous gel compositions may also be contained in the compositions of this invention providing they do not effect the stability of the present composition. Typical among these are the metal sequestering or chelating agents such as disodium EDTA (i.e. disodium ethylenediamine tetraacetic acid) to prevent product discoloration due to salicylic acid and metals interaction.

As indicated above, the procedures for treating acne in accordance with the present invention, involve a sequential or simultaneous application of the active ingredients. In both instances, the composition or compositions containing the actives are applied liberally twice a day until the lesions are cleared up. To control the condition, the composition are then applied in the same fashion; once a day as long as it is thought necessary.

The following Examples are given to further illustrate the present invention. It is to be understood, however, that the invention is not limited to these examples.

EXAMPLE 1

| Composition A Solution | % by Wt. |
| --- | --- |
| Salicylic acid | 5 |
| Ethanol | 75 |
| Water to | 100 |

| Composition B Aqueous Gel | % by Wt. |
| --- | --- |
| Benzoyl peroxide (actives) | 5.0 |
| Laureth-4 | 6.0 |
| Disodium EDTA | 0.1 |
| *Carbopol 940 | 0.5 |
| Diisopropanolamine | 0.6 |
| Water to | 100.0 |

*Carbopol 940 (Goodrich Chemical Co.) See also U.S. Pat. Nos. 3,133,865 and 2,798,053

The compositions of this Example i.e. Compositions A and B are intended for use in a sequential fashion. Each of the compositions is placed in its own dispensing container. For convenience of administration, one of each of these containers is packaged together in the same carton.

EXAMPLE 2

Aqueous Gel

| | % by Wt. |
| --- | --- |
| *Veegum K | 2.00 |
| Methocel A 4M | 1.25 |
| Disodium EDTA | 0.10 |
| **Laureth-4 | 6.00 |
| Salicylic acid | 5.00 |
| Benzoyl peroxide (approx. 70% active) | 7.79 |
| Water to | 100.00 |

*Magnesium aluminum silicate (Vanderbilt Chemical Co.)
**$CH_3(CH_2)_{10}CH_2(OCH_2CH_2)_nOH$ wherein n has an average value of 4.

The composition of this Example is used in accordance with the present invention to simultaneously apply the salicylic acid and benzoyl peroxide.

EXAMPLE 2A

Aqueous Gel

| | % by Wt. |
| --- | --- |
| Salicylic acid | 5.00 |
| Benzoyl peroxide (approx. 70% active) | 7.14 |
| Veegum K | 2.00 |
| *Methocel A 4M | 1.25 |
| **Nucol 4227 | 1.00 |
| Disodium EDTA | .10 |

| | % by Wt. |
|---|---|
| Water to | 100.00 |

*Methyl cellulose (Dow Chemical Co.)
**Cold Process Starch (modified) (Staley Starch)

The composition of this Example is also a convenient form for simultaneously applying salicylic acid and benzoyl peroxide.

EXAMPLE 2B

Aqueous Gel

| | % by Wt. |
|---|---|
| Salicylic acid | 5.00 |
| Benzoyl peroxide (approx. 70% active) | 7.30 |
| Veegum K | 3.00 |
| Methocel A 4M | 0.50 |
| Disodium EDTA | 0.10 |
| Water to | 100.00 |

This formulation afforded and acceptable but somewhat thin gel.

EXAMPLE 2C

Aqueous Gel

| | % by Wt. |
|---|---|
| Salicylic acid | 5.00 |
| Benzoyl peroxide (approx. 70% active) | 7.30 |
| Veegum K | 2.00 |
| Methocel A 4M | 2.00 |
| Disodium EDTA | 0.10 |
| Water to | 100.00 |

This formulation yielded a viscous off-white but elegant gel.

EXAMPLE 2D

Aqueous Gel

| | % by Wt. |
|---|---|
| Salicylic acid | 5.00 |
| Benzoyl peroxide (approx. 70% active) | 7.30 |
| Methocel A 4M | 4.00 |
| Disodium EDTA | 0.10 |
| Water to | 100.00 |

This formulation produced a thick white elegant gel.

EXAMPLE 2E

Example 2D was repeated only 2% Methocel A 4M was employed in lieu of the 4% utilized in said Example 2D. A less viscous but cosmetically acceptable semi-gel product was obtained.

EXAMPLE 2F

Aqueous Gel

| | % by Wt. |
|---|---|
| Salicylic acid | 5.00 |
| Benzoyl peroxide (approx. 70% active) | 7.30 |
| Veegum K | 8.00 |
| Nucol 4227 | 1.00 |
| Disodium EDTA | 0.10 |
| Water to | 100.00 |

This formulation afforded a thick smooth elegant gel.

EXAMPLE 2G

Example 2F was repeated only 4% Veegum K was employed. An unacceptable gel exhibiting slight syneresis was produced.

EXAMPLE 2H

Aqueous Gel

| | % by Wt. |
|---|---|
| Salicylic acid | 5.00 |
| Benzoyl peroxide (approx. 70% active) | 7.30 |
| Veegum K | 6.00 |
| Disodium EDTA | 0.10 |
| Water to | 100.00 |

This formulation afforded a gel product which exhibited slight syneresis. This indicates that the amount of Veegum K employed in the formulation is at the minimum level necessary to afford a satisfactory product when Veegum K is employed alone and not in conjunction with a cellulose derivative such as Methocel A 4M.

As is seen from the previous examples, Veegum K can be utilized as the sole gelling and suspending agent to afford an elegant product, providing that it is employed in a concentration of about 6% to 10% by weight, preferably 7% to 9% by weight and most preferably 8% by weight.

It has been discovered that not all Montmorillonite clay suspending and gelling agents afford chemically and physically stable aqueous gels containing Benzoyl peroxide and Salicylic acid. As seen from the following Examples 2I and 2J, the use of 8% Bentonite alone (as in Example 2I) affords an unacceptable product. Further, the use of 4% and even 8% Hectorite as in Examples 2J and 2K results in a product which loses its viscosity upon the addition of the Salicylic acid. In contrast thereto, as is shown by Example 2F, 8% Veegum K affords an exceptionally elegant product.

EXAMPLE 2I, J, and K

| | % by Wt. | | |
|---|---|---|---|
| | I | J | K |
| Salicylic acid | 5.00 | 5.00 | 5.00 |
| Benzoyl peroxide (approx. 70% active) | 7.30 | 7.30 | 7.30 |
| Hectorite | — | 8.00 | 4.00 |
| Bentonite, USP | 8.00 | — | — |
| Disodium EDTA | 0.10 | 0.10 | 0.10 |
| Water to | 100.00 | 100.00 | 100.00 |

EXAMPLE 2L

To further demonstrate that not all Montmorillonite earth suspending agents can be utilized to produce the desired chemically and physically stable gel formulations of the present invention, Example 2A was repeated only Bentonite USP was substituted for the Veegum K. The resultant product was not a gel, consequently, was considered unacceptable.

EXAMPLE 2M

Example 2A was repeated.
(a) First: omitting the Cold Process Starch;
(b) Second: omitting the Disodium EDTA;
(c) Third: omitting both the Cold Process Starch and the Disodium EDTA; and
(d) Fourth: omitting the Veegum K while increasing the Methocel A 4M from 1.3% to 3.0%.

In each case, a gel having satisfactory stability is produced. Gels (b) and (c) which did not contain a suitable sequestering agent showed discoloration, presumably, due to complex formation with salicylic acid.

Although the Cold Process Starch is not an essential component, its presence is preferred as it affords a product having exceptional feel. Gel (d) demonstrates the Veegum K does not appear to be an indispensable component providing its absence is compensated for by suitable increase in the amount of Methocel A 4M or a like cellulose derivative.

EXAMPLE 2N

Example 2A was repeated only the amount of Veegum K was varied as follows:
(a) 3% Veegum was employed; and
(b) 1% Veegum was employed.

Gel (a) though acceptable, was extremely viscous. Gel (b) was extremely thin though still a gel, indicating that the lower limit of Veegum K in Example 2A is about 1%.

EXAMPLE 2O

Example 2A was repeated only ½% Methocel A 4M was employed. The resultant product was not a gel and is considered unacceptable.

EXAMPLE 2P

The following Examples were carried out to ascertain whether cellulose derivatives other than Methocel A 4M could be employed in place of the Methocel A 4M in the preferred composition of Example 2A.

(a) Example 2A was repeated only the Methocel A 4M was replaced with a like quantity of hydroxypropyl cellulose (Klucel HF-Hercules Chemical Co.).

A highly unsatisfactory product resulted presumably due to incompatibility with the Salicylic acid.

(b) Example 2A was repeated only the Methocel A 4M was replaced by:
(i) a like quantity of hydroxypropyl methyl cellulose. (Methocel E 4M-Dow Chemical);
(ii) by 2% hydroxypropyl methyl cellulose;
(iii) by 3% hydroxypropyl methyl cellulose; and
(iv) by 4% hydroxpropyl methyl cellulose.

Gels (i)–(iv) were all acceptable thick smooth gels.
It was noted that viscosity of the gel increases with increase in concentration of the Hydroxypropyl methyl cellulose.

(c) Example 2A was repeated only the Veegum K was omitted and the Methocel A 4M was replaced by:
(i) 3% hydroxypropyl methyl cellulose;
(ii) 4% hydroxypropyl methyl cellulose; and
(iii) 5% hydroxypropyl methyl cellulose.

In each case an acceptable thick white gel was obtained.

Confirming the finding that Veegum K can be omitted from preferred formulation 2A and relaced by a suitable quantity of either hydroxypropyl methyl cellulose or Methocel A 4M.

EXAMPLE 2Q

Example 2A was repeated only the Veegum K was omitted and the Methocel A 4M was replaced by:
(i) 2% hydroxy ethyl cellulose (Natrosol 250-HHR Hercules Chemical Co.); and
(ii) 4% hydroxy ethyl cellulose.

In each case, (i) and (ii), a gel could not be produced.

EXAMPLE 2R

Aqueous Gel

|  | % by Wt. |
| --- | --- |
| Salicylic acid | 5.13 |
| Benzoyl Peroxide (72.37% active) | 7.16 |
| Xanthan Gum (Keltrol - Kelco Co.) | 2.00 |
| Disodium EDTA | 0.10 |
| Water to | 100.00 |

An acceptable smooth white gel was obtained.

EXAMPLE 2S (i) Example 2R was repeated only 5% Xanthan Gum was employed. An acceptable viscous gel was obtained.
(ii) Example 2R was repeated only the amount of Xanthan Gum was reduced to 1% by weight and 1% by weight Veegum K was added. An acceptable gel was obtained.

Xanthan and Veegum K may be employed as the thickening and suspending agent in the compositions of the present invention in a Xanthan to Veegum K ratio of respectively 2 to 3:1.

Ideally from 1 to 3% by weight Xanthan is employed with from ½ to 1% by weight of Veegum K.

EXAMPLE 2T

Example 2A was repeated only in place of the Veegum K and Methocel A 4M one of the following thickening and suspending agents was employed:
(i) 4% by wt. Polyethylene Oxide (having an average molecular weight of about 400,000-Polyox WSRN 3000-Union Carbide);
(ii) 6% by wt. Polyethylene Oxide (Polyox WSRN 3000);
(iii) 5% by wt. Polyethylene Oxide (having an average molecular weight of about 300,000-Poly WSRN-750-Union Carbide);
(iv) 7% by wt. Polyethylene Oxide (Polyox WSRN-750);
(v) 3% by wt. Polyethylene Oxide (having an average molecular weight of about 600,000-Polyox WSR-205-Union Carbide);
(vi) 5% by wt. Polyethylene Oxide (Polyox WSR-205);
(vii) 1% by wt. Pectin N.F. (Hercules);
(viii) 3% by wt. Pectin N.F.
(ix) 1% by wt. Polyacrylamide (e.g. Gelamide 250-American Cyanamide);
(x) 3% by wt. Polyacrylamide;

(xi) 1% by wt. of a 1:1 mixture of Hectorite and Hydroxyethyl cellulose (Bentone LT-National Lead); and (xii) 3% by wt. of a 1:1 mixture of Hectorite and Hydroxyethyl cellulose.

All of formulations (i)-(xii) produced acceptable and stable gels.

EXAMPLE 3

Benzoyl Peroxide/Salicylic Acid Sequential Application in the Treatment of Acne Vulgaris Method:

Three treatments were compared in three groups of 50 adolescents with moderate acne vulgaris. The subjects had numerous open and closed comedones with a variable quantity of papules and pustules. The agents were applied twice daily for 8 weeks; the effect of treatment was assessed globally according to a widely used conventional schema:

poor = less than 25% improvement or worse
fair = 26% to 50% improvement
good = 51% to 75% improvement
excellent = greater than 75% to clear The treatments were: (1) 5% salicylic acid in 75% aqueous ethanol (Composition A, Example 1); (2) 5% benzoyl peroxide gel (Composition B, Example 1); (3) 5% salicylic acid (Composition A, Example 1) followed immediately by 5% benzoyl peroxide gel (Composition B, Example 1).

Results and Conclusions:

The data are summarized in Table I below.

Benzoyl peroxide alone was somewhat superior to salicylic acid alone. Both were moderately effective. The sequence of salicylic acid and benzoyl peroxide was clearly superior to either agent alone. The response was also swifter. The latter is important to maintain patient compliance. Papulo-pustules in particular regressed more rapidly with the combination. The drying effect was also greater and this was perceived as desirable in overcoming oiliness.

All three treatments were well tolerated though temporary redness was more frequent with the combination. No subject dropped out of the study or thought the treatments too severe.

TABLE I

| COMPARATIVE EFFICACY IN ACNE | | | | |
|---|---|---|---|---|
| | Excellent | Good | Fair | Poor |
| Salicylic acid | 3% | 39% | 44% | 14% |
| Benzoyl peroxide | 8% | 46% | 39% | 7% |
| Salicylic acid plus benzoyl peroxide | 14% | 61% | 23% | 2% |

As pointed out previously, one of the features in the pathology of acne vulgaris is the formation of comedones. Any therapy that has a comedolytic effect should be beneficial in the treatment of this condition. The following Example demonstrates the comedolytic effect of a therapy that utilizes salicylic acid and benzoyl peroxide and further demonstrates that it is more effective for this purpose than the use of either alone.

EXAMPLE 4

Comedolytic Effect in Rabbit Ears

Method:

Comedones were induced in both external ear canals of albino rabbits by the daily application for two weeks of 5% crude coal tar ointment.

The test agents were then applied once daily for two weeks to opposite sides. A group of five rabbits was used for each test. The tissue was biopsied and horizontally sectioned. The size of the comedones (follicular hyperkeratosis) was estimated under the microscope according to the following scale:

0 = none
1 = slight comedones
2 = moderate comedones
3 = large comedones

The treatment groups were as follows: (1) 5% benzoyl peroxide gel (Composition B, Example 1) vs. 5% ethanolic salicylic acid (Composition A, Example 1) followed immediately by 5% benzoyl peroxide gel (Composition B, Example 1); (2) 5% ethanolic salicylic acid (Composition A, Example 1) vs. 5% ethanolic salicylic acid (Composition A, Example 1) followed immediately by 5% benzoyl peroxide gel (Composition B, Example 1).

Results:

The results are summarized in Tables II and III below. In both comparisons, the comedones were unequivocally smaller on the combination side. It can be seen that salicylic acid alone is more comedolytic than benzoyl peroxide.

TABLE II

| 5% Benzoyl Peroxide vs. Sequential 5% Salicylic Acid and 5% Benzoyl Peroxide | | |
|---|---|---|
| Rabbit No. | 5% Benzoyl Peroxide | Combination |
| 1 | 2 | 1 |
| 2 | 2 | 1 |
| 3 | 1 | 0 |
| 4 | 3 | 1 |
| 5 | 2 | 0 |
| mean: | 2.0 | 0.6 |

TABLE III

| 5% Salicylic Acid vs. Sequential 5% Salicylic Acid and 5% Benzoyl Peroxide | | |
|---|---|---|
| Rabbit No. | 5% Salicylic Acid | Combination |
| 1 | 1 | 0 |
| 2 | 1 | 1 |
| 3 | 2 | 1 |
| 4 | 2 | 1 |
| 5 | 1 | 0 |
| mean: | 1.4 | 0.6 |

As also indicated above, another feature of the pathology of acne vulgaris is the inflammation that results from the rupture of comedones. The acne bacillus, *Propionibacterium acnes*, plays an important causal role first in contributing to the formation of comedones and then by producing toxic products that cause their rupture. Any agent which reduces the level of these organisms within the follicles should have a beneficial effect in the treatment of acne. The following Example shows that the combination of salicylic acid and benzoyl peroxide greatly reduces the quantity of *Propionibacterium acnes* on the skin. Five percent benzoyl peroxide alone is a highly effective agent in reducing the density of *Propionibacterium acnes*, being more than 95% effective. It would hardly be expected that the combination of salicylic acid and benzoyl peroxide would be superior to benzoyl peroxide alone. The combination would have to be at least as effective as benzoyl peroxide alone in reducing *Propionibacterium acnes*. This is in fact the case as is demonstrated in Example 5 below (compare Tables IV and V). However, although benzoyl peroxide alone is equivalent to the combination as as antibacterial agent, this is only one aspect for measuring the effectiveness of these materials in the treatment of acne vulgaris. As already pointed out above by the least two other parameters, that are important in the treatment of acne vulgaris, the combination of salicylic acid and benzoyl peroxide were found to be superior to either salicylic acid or benzoyl peroxide alone.

EXAMPLE 5

Comparison of Anti-microbial Effect of 5% Benzoyl Peroxide alone and 5% Benzoyl Peroxide in Sequence with 5% Ethanolic Solution of Salicylic Acid Method:

Two groups of ten healthy young adult black males were studied. These were selected because of facial characteristics associated with high levels of *Propionibacterium acnes;* namely, bright follicular fluorescence under the Woods light and excessive oiliness.

The detergent scrub method was utilized to determine the density of *Propionibacterium acnes* on the cheeks. Samples were taken before and again after one and two weeks of treatment.

The first group received 5% benzoyl peroxide gel (Composition B, Example 1) to the entire face twice daily for two weeks. In the second group, 5% salicylic acid solution (Composition A, Example 1) was applied twice daily, followed immediately each time with 5% benzoyl peroxide gel (Composition B, Example 1).

It should be noted that a third group of ten subjects received 5% salicylic acid alone. There was no effect on the density of *Propionibacterium acnes;* hence the data are not given.

TABLE IV

| | 5% Benzoyl Peroxide Gel Density of *Propionibacterium Acnes* (millions/cm²) | | |
|---|---|---|---|
| | Control | Treatment | |
| Subject No. | Pre-Treatment | Week One | Week Two |
| 1 | 6.5 | 5.3 | 3.9 |
| 2 | 6.3 | 3.6 | 3.5 |
| 3 | 4.4 | 2.2 | 2.0 |
| 4 | 5.6 | 4.2 | 3.7 |
| 5 | 6.2 | 2.7 | 3.0 |
| 6 | 5.5 | 4.2 | 3.6 |
| 7 | 7.0 | 4.9 | 4.5 |
| 8 | 5.4 | 3.7 | 3.2 |
| 9 | 7.1 | 4.3 | 4.0 |
| 10 | 6.3 | 5.1 | 5.3 |
| mean: | 6.03 | 4.02 | 3.67 |

TABLE V

| | Sequence of 5% Salicylic Acid and 5% Benzoyl Peroxide Gel Density of *Propionibacterium Acnes* (millions/cm²) | | |
|---|---|---|---|
| | Control | Treatment | |
| Subject No. | Pre-Treatment | Week One | Week Two |
| 1 | 5.5 | 4.1 | 3.2 |
| 2 | 5.7 | 4.4 | 3.1 |
| 3 | 5.5 | 2.5 | 2.8 |
| 4 | 5.9 | 4.7 | 3.9 |
| 5 | 5.2 | 3.7 | 3.0 |
| 6 | 4.6 | 3.4 | 2.9 |
| 7 | 6.1 | 4.2 | 3.2 |
| 8 | 5.6 | 5.3 | 4.6 |
| 9 | 6.5 | 2.3 | 2.5 |
| 10 | 6.3 | 4.3 | 5.1 |
| mean: | 5.69 | 3.89 | 3.43 |

The following Example illustrates the utility of the simultaneous application of 5% salicylic acid and 5% benzoyl peroxide in an aqueous gel composition. In these tests, the antibacterial effect of this combination on *Propionibacterium acnes* was examined.

EXAMPLE 6

Method:

The composition of Example 2A was applied twice daily for two weeks to the faces of ten healthy, young adult black males with oily skin. *Propionibacterium acnes* densities were determined before and again after one and two weeks of treatment. The results are summarized in Table VI.

Results:

These show that the reduction of *Propionibacterium acnes* with the combination was rather similar to that previously obtained with application of each agent in sequence. On the average, the *Propionibacterium acnes* population was reduced by 95% and more. The mixing of these two agents in one formulation does not result in loss of the desired effect although it takes somewhat longer to reach this effect.

TABLE VI

| | Combination of 5% Salicylic Acid and 5% Benzoyl Peroxide in a Gel Product (millions/cm²) | | |
|---|---|---|---|
| | Control | Treatment | |
| Subject No. | Pre-Treatment | Week One | Week Two |
| 1 | 6.3 | 4.8 | 4.6 |
| 2 | 5.5 | 4.2 | 3.5 |
| 3 | 4.8 | 3.8 | 3.2 |
| 4 | 5.9 | 5.0 | 3.7 |
| 5 | 7.0 | 4.6 | 3.6 |
| 6 | 6.4 | 5.2 | 4.3 |
| 7 | 5.2 | 4.1 | 2.4 |
| 8 | 5.7 | 5.0 | 3.6 |
| 9 | 6.1 | 4.3 | 2.5 |
| 10 | 5.5 | 3.6 | 3.0 |
| mean: | 5.8 | 4.5 | 3.4 |

What is claimed is:

1. A topical, therapeutic composition comprising from about 3% to about 7% salicylic acid and from 3% to about 20% benzoyl peroxide in a pharmaceutically acceptable vehicle comprising an aqueous gel containing an amount sufficient to produce a stable gel of a gelling and thickening agent selected from the group consisting of a mixture of about 1 to about 3% by weight magnesium aluminum silicate with about 1 to about 3% by weight of methyl cellulose, wherein the combined amount of the magnesium aluminum silicate and the methyl cellulose does not exceed about 5% by weight; about 7 to about 9% by weight of magnesium aluminum silicate; about 2 to about 5% by weight methyl cellulose; about 1 to about 3% by weight pectin; about 2 to about 4% by weight xanthan gum; about 4 to about 6% by weight polyethylene oxide having an average molecular weight of about 400,000; about 5 to about 7% by weight polyethylene oxide having an average molecular weight of about 300,000; about 3 to about 5% by weight polyethylene oxide having an average molecular weight of about 600,000; about 1 to about 3% by weight polyacrylamide; and about 2 to about 4% by weight of a 1:1 mixture of hectorite and hydroxyethylcellulose.

2. A composition according to claim 1 containing about 5% salicylic acid and 5% benzoyl peroxide.

3. A composition according to claim 1 wherein said agent is a mixture of about 2% by weight of magnesium aluminum silicate and about 1.25% by weight of methylcellulose.

4. A composition according to claim 3 further including about 1% by weight of modified cold process starch.

5. A composition according to claim 4 further including an amount of a sequestering agent sufficient to sequester metal ions present in the composition which may complex with the salicylic acid and promote decomposition of the benzoyl peroxide.

6. The composition according to claim 5 wherein the sequestering agent is disodium EDTA or EDTA and is present in an amount of about 0.1% by weight.

7. A composition according to claim 6 further including about 6% by weight of a compound having the formula $CH_3(CH_2)_{10}CH_2(OCH_2CH_2)_nOH$ wherein n has an average value of 4.

8. A composition according to claim 1 wherein said agent is magnesium aluminum silicate and is present in an amount of about 8% by weight.

9. A composition according to claim 1 wherein said agent is methylcellulose and is present in an amount of about 3 to 4% by weight.

10. A composition according to claim 1 wherein said agent is pectin and is present in an amount of about 2% by weight.

11. A composition according to claim 1 wherein said agent is xanthan gum and is present in an amount of about 3% by weight.

12. A composition according to claim 1 wherein said agent is polyethylene oxide having an average molecular weight of about 400,000, and is present in an amount of about 5% by weight.

13. A composition according to claim 1 wherein said agent is polyethylene oxide having an average molecular weight of about 300,000 and is present in an amount of about 6% by weight.

14. A composition according to claim 1 wherein said agent is polyethylene oxide having an average molecular weight of about 600,000 and is present in an amount of about 6% by weight.

15. A composition according to claim 1 wherein said agent is polyacrylamide and is present in an amount of about 2% by weight.

16. A composition according to claim 1 wherein said agent is a 1:1 mixture of hectorite and hydroxyethylcellulose and is present in an amount of about 3% by weight.

* * * * *